US00PP17746P3

(12) United States Plant Patent
Wicki

(10) Patent No.: US PP17,746 P3
(45) Date of Patent: May 22, 2007

(54) *AGROSTIS* PLANT NAMED 'GREEN TWIST'

(50) Latin Name: *Agrostis stolonifera*
Varietal Denomination: Green Twist

(75) Inventor: Eidg. Dipl. Gärtnermeister Wicki, Auboden (CH)

(73) Assignees: Heinrich Westhoff (DE); Josef Westhoff (DE)

( * ) Notice: Subject to any disclaimer, the term of this patent is extended or adjusted under 35 U.S.C. 154(b) by 0 days.

(21) Appl. No.: 10/600,946

(22) Filed: Jun. 20, 2003

(65) Prior Publication Data

US 2004/0261151 P1 Dec. 23, 2004

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent Bell
*Assistant Examiner*—Annette H Para
(74) *Attorney, Agent, or Firm*—The Webb Law Firm

(57) ABSTRACT

A new and distinct early flowering *Agrostis* plant with intense green leaves and a cascading habit.

2 Drawing Sheets

Botanical classification: *Agrostis stolonifera.*
Varietal denomination: 'Green Twist'.

BACKGROUND OF THE INVENTION

The present invention comprises a new and distinct cultivar of *Agrostis* plant known by the varietal name 'Green Twist'. The new variety was discovered between the years 1998–2000 in a selected breeding program in Ausbildungsstätte Auboden, Brunnadern, Switzerland designed to produce a new variety of *Agrostis* with nice structural characteristics and a long weeping growth habit. The new variety was chosen from a group of unknown, unpatented breeding plants from a selected breeding program. The new variety was first asexually reproduced in 2000 by cuttings in Switzerland. The new variety has been trial and field tested at Ostalpen and has been found to retain its distinctive characteristics and remain true to type through successive propagations.

'Green Twist' is similar to other *Agrostis* varieties in the breeding program in leaf color, leaf form, and stem color. 'Green Twist' is different from other *Agrostis* varieties in the breeding program in that 'Green Twist' is longer weeping, is mildew resistant, and is sterile.

The following traits also distinguish 'Green Twist' as a new and distinct cultivar:

1. 'Green Twist' is a beautiful structural plant.
2. 'Green Twist' has a cascading and extraordinarily long growth habit.
3. 'Green Twist' does not bloom.
4. 'Green Twist' has intense green linear leaves.
5. 'Green twist' has light green, wavy, curved culms.

DESCRIPTION OF THE DRAWING

The accompanying photographic drawing illustrates the new variety, with the color being as nearly true as is possible with color illustrations of this type.

DESCRIPTION OF THE PLANT

Figure 1:
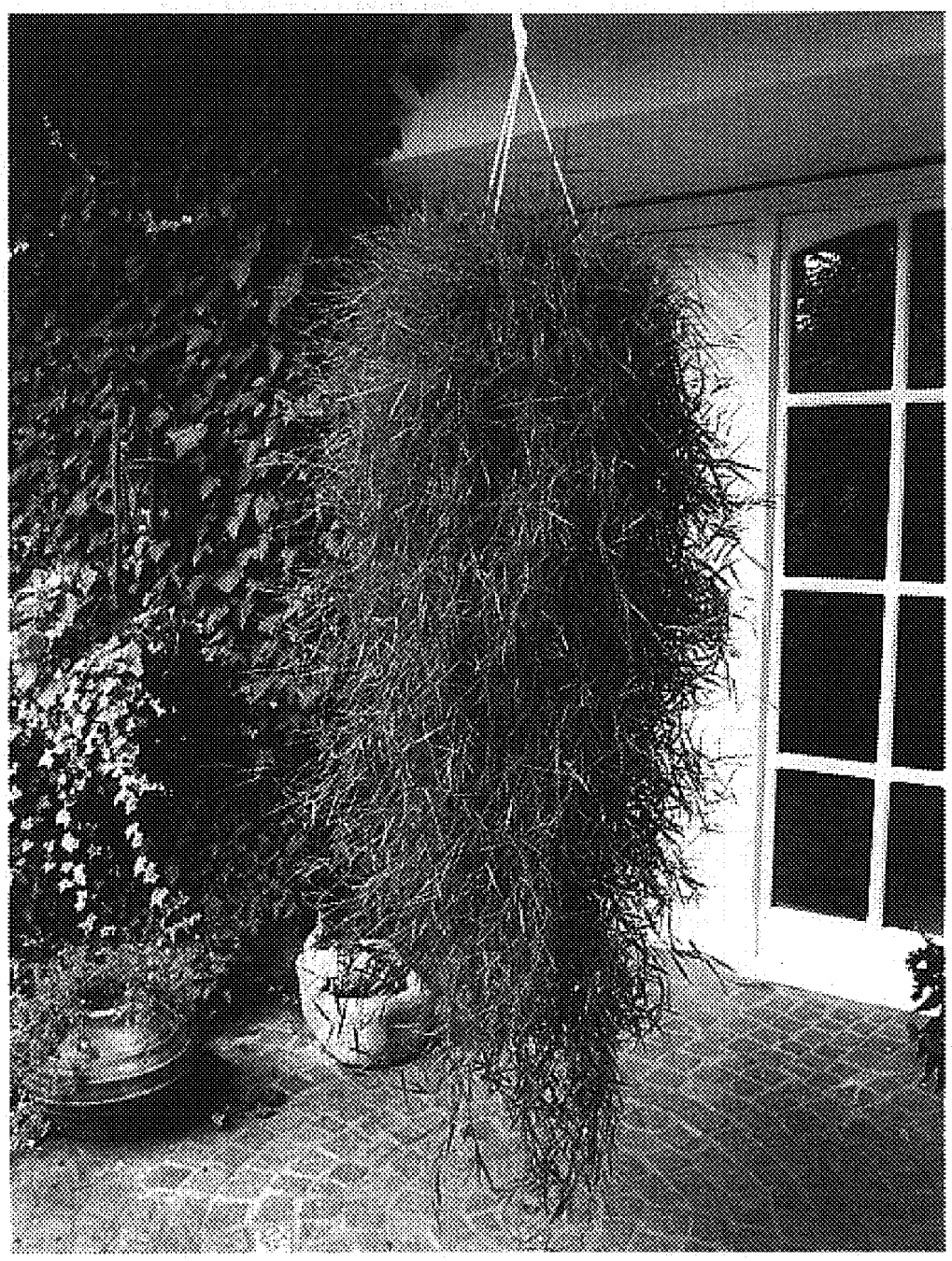
FIG. 1 is a photograph of the whole plant.
Figure 2:
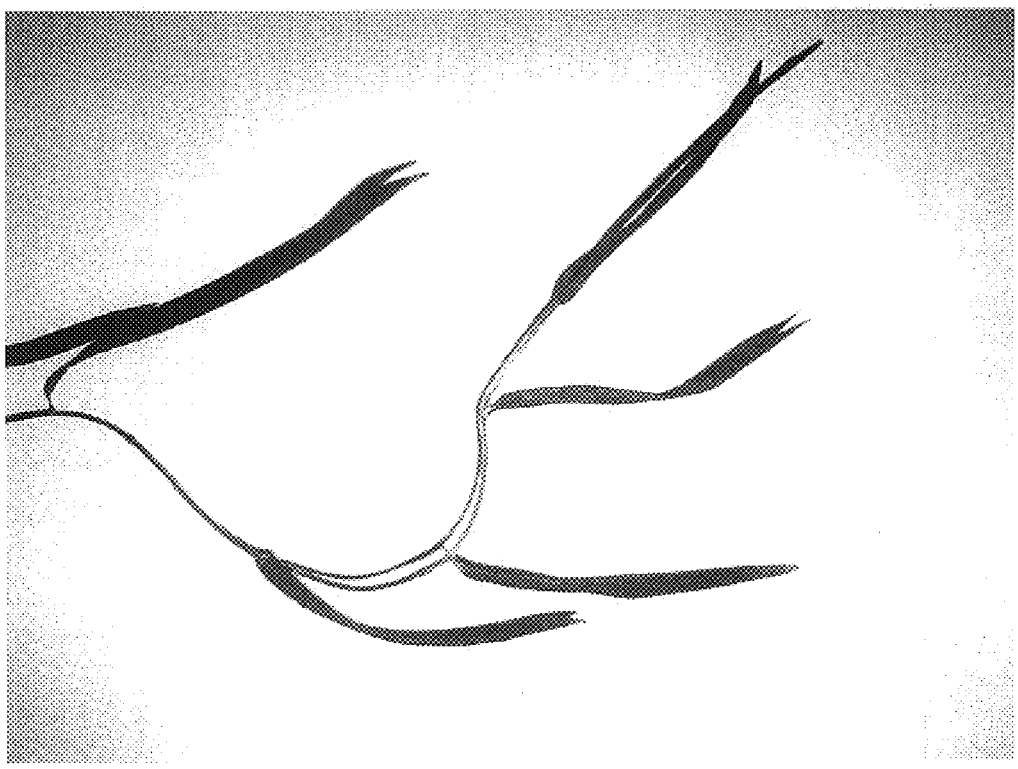
FIG. 2 is a close-up view of the culms of the new variety.

The following detailed description sets forth characteristics of the new cultivar. The data which defines these characteristics were collected by asexual reproductions by cuttings carried out in Germany. Plants for the description were grown in a 25 cm pots and were 28 weeks old. Flowering plants were grown in a greenhouse and outside at a temperature range of 10–25° C. The color readings were taken in a greenhouse and outside under natural light. Color references are primarily to the 2001 R.H.S. Colour Chart of the Royal Horticultural Society of London.

PLANT

Height: 20 cm.
Diameter: 58 cm in a 25 cm pot.
Length: 1.7 m average; can grow longer than 2 m.
Vigor: Abundant.
Roots:
- *Source.*—Surface runners (bot not rhizomes); Roots build from each node that makes soil contact.
- *Form.*—Very fine; branched; dense.
- *Time to initiate roots.*—6–8 days at 18–20 ° C.
- *Time to develop roots.*—14–18 days at 18–20° C.

Time to produce a finished plant from a rooted cutting: 10–12 weeks in a 11 cm container.

Culms:
- *Form.*—Hanging; weeping.
- *Diameter.*—0.5–1 mm (between the nodes).
- *Shape.*—Cylindrical.
- *Length.*—Main culms: 0.9–1.4 m. Lateral culms: 15–60 cm.
- *Color.*—144C.
- *Internode length.*—4.7 cm.
- *Texture.*—Smooth.
- *Pubescence.*—Glabrous.

*Arrangement.*—Abundant; long weeping; very few branching culms at nearly every node until midway up the main branch (from soil); culms are wavy so the leaves grow into different directions.

Plantlets:

*Diameter.*—14.6 cm on cuttings 2 weeks old.

*Average length.*—Cuttings 2 weeks old: 12 cm. Plantlets 8–10 weeks old: 20 cm.

*Internode length.*—Cuttings 2 weeks old: 3.5–4.5 cm. Plantlets 8–10 weeks old: All nodes root on the soil and form new shoots.

*Texture.*—Smooth.

*Pubescence.*—Glabrous.

*Color.*—Cuttings 2 weeks old: 144A. Plantlets 8–10 weeks old: 143A.

Foliage:

*Arrangement.*—Alternate.

*Leaf blades.*—Shape: Linear. Number: One per node. Width: 0.6 cm. Length: 11.6 cm from sheath. Shape of apex: Acute. Shape of base: Develops from the sheath which encloses the culm and arises from the node. Texture: Dull. Aspect: Flat; some twisted. Margin type: Entire. Venation: Parallel. Pubescence: Upper surface: Glabrous. Lower surface: Glabrous.

*Color.*—Young leaf blade: Upper surface: Between 137B and 137C. Lower surface: Between 137B and 137C. Mature leaf blade: Upper surface: 137A. Lower surface: 137A.

Ligules:

*Length.*—1.2 mm.

*Width.*—3 mm; encloses half of the culm.

*Shape.*—Very thin; short; two-dimensional.

*Color.*—Translucent; 149D.

*Pubescence.*—Glabrous.

*Number.*—One ligule per leaf.

Sheaths:

*Length.*—2.5–4.2 cm; average 3.4. cm.

*Width.*—3–4 mm.

*Shape.*—Linear; encloses the culm.

*Color.*—Near the node: 145C; anthocyanin 200D may be present. Near the leaf blade: Between 145A and 145B.

*Petiole.*—None; leaves grow direct from the node with a leaf sheath and a leaf blade.

*Veins.*—Venation: Parallel. Color: Same as leaf.

FLOWERS

Flowers: None present.

REPRODUCTIVE ORGANS

Reproductive organs: None present.

GENERAL

Cold tolerance: 'Green Twist' is tolerant to cold until the temperature is −5° C. and lower. From −12° C. 'Green Twist' may lose its leaves, but the plant will hardily regenerate in the Spring.

Drought tolerance: 'Green Twist' is not drought tolerant. The new variety requires a steady, high water supply.

Mildew resistance: 'Green Twist' is mildew resistant.

Plant diseases: None observed.

Insect susceptibility: None observed.

I claim:

1. A new and distinct variety of *Agrostis* plant substantially as shown and described.

* * * * *